United States Patent
Flanagan et al.

(10) Patent No.: US 7,803,805 B2
(45) Date of Patent: *Sep. 28, 2010

(54) CRISTALLINE 3-{(3R,4R)-4 METHYL-3-[METHYL-(7H-PYRROLO[2,3-D]PYRIMIDIN-4-YL)-AMINO]-PIPERIDIN-1-YL}-3-OXO-PROPIONITRILE MONO CITRATE SALT

(75) Inventors: Mark E. Flanagan, Gales Ferry, CT (US); Zheng J. Li, Quaker Hill, CT (US)

(73) Assignee: Pfizer Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/032,990

(22) Filed: Jan. 10, 2005

(65) Prior Publication Data

US 2005/0159434 A1   Jul. 21, 2005

Related U.S. Application Data

(63) Continuation of application No. 10/310,078, filed on Dec. 4, 2002, now Pat. No. 6,965,027.

(60) Provisional application No. 60/338,984, filed on Dec. 6, 2001.

(51) Int. Cl.
 A61P 37/06   (2006.01)
 A61P 11/06   (2006.01)
 C07D 487/04  (2006.01)
 A61K 31/519  (2006.01)

(52) U.S. Cl. .................... 514/265.1; 544/280
(58) Field of Classification Search ............... 544/280; 514/265.1
 See application file for complete search history.

(56) References Cited

U.S. PATENT DOCUMENTS

| | | | |
|---|---|---|---|
| 5,389,509 A | 2/1995 | Maskasky | |
| 5,686,457 A | 11/1997 | Traxler et al. | |
| 6,080,747 A | 6/2000 | Uckun et al. | |
| 6,136,595 A | 10/2000 | Ihle et al. | |
| 6,180,636 B1 | 1/2001 | Traxler et al. | |
| 6,187,552 B1 | 2/2001 | Roberds et al. | |
| 6,627,754 B2 * | 9/2003 | Blumenkopf et al. | 544/280 |
| 6,956,041 B2 * | 10/2005 | Blumenkopf et al. | 514/258.1 |
| 6,965,027 B2 * | 11/2005 | Flanagan et al. | 544/280 |
| 7,091,208 B2 * | 8/2006 | Blumenkopf et al. | 514/259.1 |
| 2001/0053782 A1 | 12/2001 | Blumenkopf et al. | |
| 2003/0073719 A1 | 4/2003 | Wilcox et al. | |
| 2004/0053947 A1 | 3/2004 | Blumenkopf et al. | |
| 2007/0292430 A1 * | 12/2007 | Blumenkopf et al. | 424/141.1 |

FOREIGN PATENT DOCUMENTS

| | | |
|---|---|---|
| WO | WO 9965908 | 12/1999 |
| WO | WO 9965909 | 12/1999 |
| WO | WO 0142246 | 6/2001 |
| WO | WO 02096909 | 12/2002 |

OTHER PUBLICATIONS

Groom, Colin R. et al, Drug Discovery Today, vol. 7, No. 15, 2002, pp. 801-802.*
Hong, J.C. et al, Semin. Nephrol., vol. 20, No. 2, 2000, pp. 108-125.*
Malaviya, R. et al, Pharm. Exper. Therap., vol. 295, No. 3, 2000, pp. 912-926.*
Palmer Trends in Pharmacological Sciences 23(9) 426-433 Sep. 2002.*
Berge et. al. (Journal of Pharmaceutical Sciences, 1977, 66(1), pp. 1-19).*
Baldwin et al, J. of Heart and Lung Transplantation, vol. 20(2), pp. 155-156 (2001), abstract.
Hartinick et al, Ann Otol. rhinol. Laryngol., 109(1):45-7 (2000), abstract.

* cited by examiner

*Primary Examiner*—James O Wilson
*Assistant Examiner*—Susanna Moore
(74) *Attorney, Agent, or Firm*—Ram W. Sabnis

(57) ABSTRACT

This invention relates to novel amorphous and crystalline forms of 3-{(3R,4R)-4-methyl-3-[methyl-(7H-pyrrolo[2,3-d]pyrimidin-4-yl)-amino]-piperidin-1-yl}-3 -oxo-propionitrile mono citrate salt, useful as inhibitors of protein kinases, and to their methods of preparation.

9 Claims, 2 Drawing Sheets

DSC thermogram

CRISTALLINE 3-{(3R,4R)-4 METHYL-3-[METHYL-(7H-PYRROLO[2,3-D]PYRIMIDIN-4-YL)-AMINO]-PIPERIDIN-1-YL}-3-OXO-PROPIONITRILE MONO CITRATE SALT

CROSS-REFERENCE TO RELATED APPLICATIONS

This application is a continuation of U.S. patent application Ser. No. 10/310,078, filed Dec. 4, 2002 which claims benefit of priority under 35 U.S.C. §119 (e) to U.S. Provisional Application No. 60/338,984, filed on Dec. 6, 2001 which is herein incorporated by reference in its entirety.

BACKGROUND OF THE INVENTION

This invention relates to a novel crystalline form of 3-{(3R,4R)-4-methyl-3-[methyl-(7H-pyrrolo[2,3-d]pyrimidin-4-yl)-amino]-piperidin-1-yl}-3-oxo-propionitrile mono citrate salt and to its method of preparation.

3-{(3R,4R)-4-methyl-3-[methyl-(7H-pyrrolo[2,3-d]pyrimidin-4-yl)-amino]-piperidin-1-yl}-3-oxo-propionitrile has the chemical formula $C_{16}H_{20}N_6O$ and the following structural formula

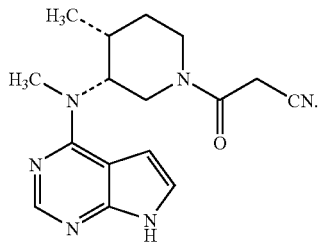

II

Its synthesis is described in co-pending U.S. patent application Ser. No. 09/732,669, filed Dec. 8, 2000 and U.S. provisional patent application Ser. No. 60/294,775, filed May 31, 2001, commonly assigned to the assignee of the present invention and which are incorporated herein by reference in their entirety. 3-{(3R,4R)-4-methyl-3-[methyl-(7H-pyrrolo[2,3-d]pyrimidin-4-yl)-amino]-piperidin-1-yl}-3-oxo-propionitrile, and its corresponding citrate salt, are useful as inhibitors of protein kinases, such as the enzyme Janus Kinase 3 (hereinafter also referred to as JAK3) and as such are useful therapy as immunosuppressive agents for organ transplants, xeno transplation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

The crystalline form of 3-{(3R,4R)-4-methyl-3-[methyl-(7H-pyrrolo[2,3-d]pyrimidin-4-yl)-amino]-piperidin-1-yl}-3-oxo-propionitrile mono citrate salt was determined to have solid state properties which are acceptable to support tablet development.

The present invention is also directed to processes for preparing crystalline 3-{(3R,4R)-4-methyl-3-[methyl-(7H-pyrrolo[2,3-d]pyrimidin-4-yl)-amino]-piperidin-1-yl}-3-oxo-propionitrile mono citrate salt.

SUMMARY OF THE INVENTION

This invention relates to a novel crystalline form of 3-{(3R,4R)-4-methyl-3-[methyl-(7H-pyrrolo[2,3-d]pyrimidin-4-yl)-amino]-piperidin-1-yl}-3-oxo-propionitrile mono citrate salt which is useful in (a) treating or preventing a disorder or condition selected from organ transplant rejection, xeno transplation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, leukemia and other autoimmune diseases or (b) the inhibition of protein kinases or Janus Kinase 3 (JAK3) in a mammal, including a human. The novel crystalline form melts at a temperature of about 203° C. to about 210° C., and exhibits an X-ray diffraction pattern with characteristic peaks expressed in degrees 2-theta (2θ) at 5.7, 16.1, 20.2 and 20.5, as depicted in FIG. 1. A discussion of the theory of X-ray powder diffraction patterns can be found in Stout & Jensen, *X-Ray Structure Determination; A Practical Guide*, MacMillan Co., New York, N.Y. (1968), which is incorporated by reference in its entirety.

This invention also relates to the crystalline form of 3-{(3R,4R)-4-methyl-3-[methyl-(7H-pyrrolo[2,3-d]pyrimidin-4-yl)-amino]-piperidin-1-yl}-3-oxo-propionitrile mono citrate salt with a differential scanning calorimetry thermogram, as depicted in FIG. 2, having a characteristic peak at a temperature between about 203° C. to about 210° C., having an onset at a temperature between about 199° C. to about 206° C. at a scan rate of 5° C. per minute.

The invention also relates to an amorphous form of 3-{(3R,4R)-4-methyl-3-[methyl-(7H-pyrrolo[2,3-d]pyrimidin-4-yl)-amino]-piperidin-1-yl}-3-oxo-propionitrile mono citrate salt.

The present invention also relates to a pharmaceutical composition for (a) treating or preventing a disorder or condition selected from organ transplant rejection, xeno transplation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia, and other autoimmune diseases or (b) the inhibition of protein kinases or Janus Kinase 3 (JAK3) in a mammal, including a human, comprising an amount of a compound of formula I, effective in such disorders or conditions and a pharmaceutically acceptable carrier.

The present invention also relates to a method for the inhibition of protein tyrosine kinases or Janus Kinase 3 (JAK3) in a mammal, including a human, comprising administering to said mammal an effective amount of a compound of formula I.

The present invention also relates to a method for treating or preventing a disorder or condition selected from organ transplant rejection, xeno transplation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia, and other autoimmune diseases in a mammal, including a human, comprising administering to said mammal an amount of a compound of formula I, effective in treating such a condition.

The present invention also relates to a process for for preparing 3-{(3R,4R)4-methyl-3-[methyl-(7H-pyrrolo[2,3-d]pyrimidin-4-yl)-amino]-piperidin-1-yl}-3-oxo-propionitrile mono citrate salt comprising reacting 3-{(3R,4R)-4-methyl-3-[methyl-(7H-pyrrolo[2,3-d]pyrimidin-4-yl)-amino]-piperidin-1-yl}-3-oxo-propionitrile with citric acid.

DETAILED DESCRIPTION OF THE INVENTION

Figure 1:
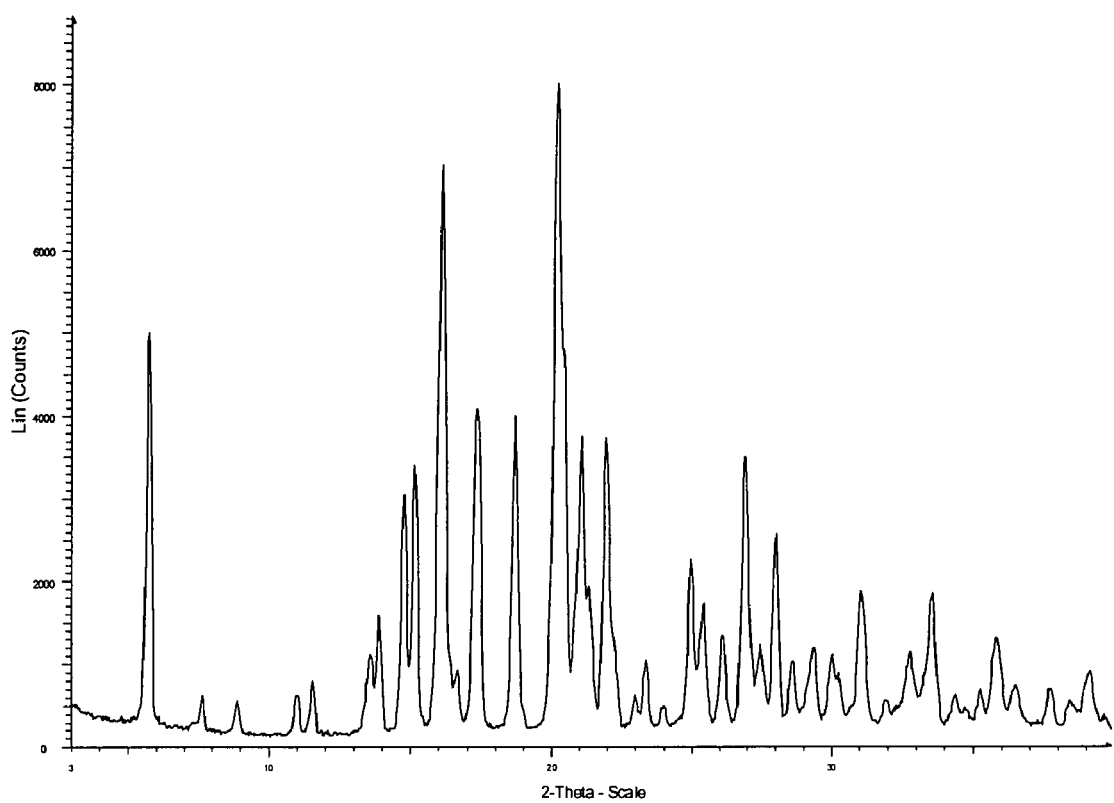
FIG. 1 is a characteristic X-ray powder diffraction pattern for 3-{(3R,4R)-4-methyl-3-[methyl-(7H-pyrrolo[2,3-d]pyrimidin-4-yl)-amino]-piperidin-1-yl}-3-oxo-propionitrile mono citrate salt. (Vertical Axis: Intensity (counts); Horizontal Axis: Two Theta (Degrees)).
Figure 2:
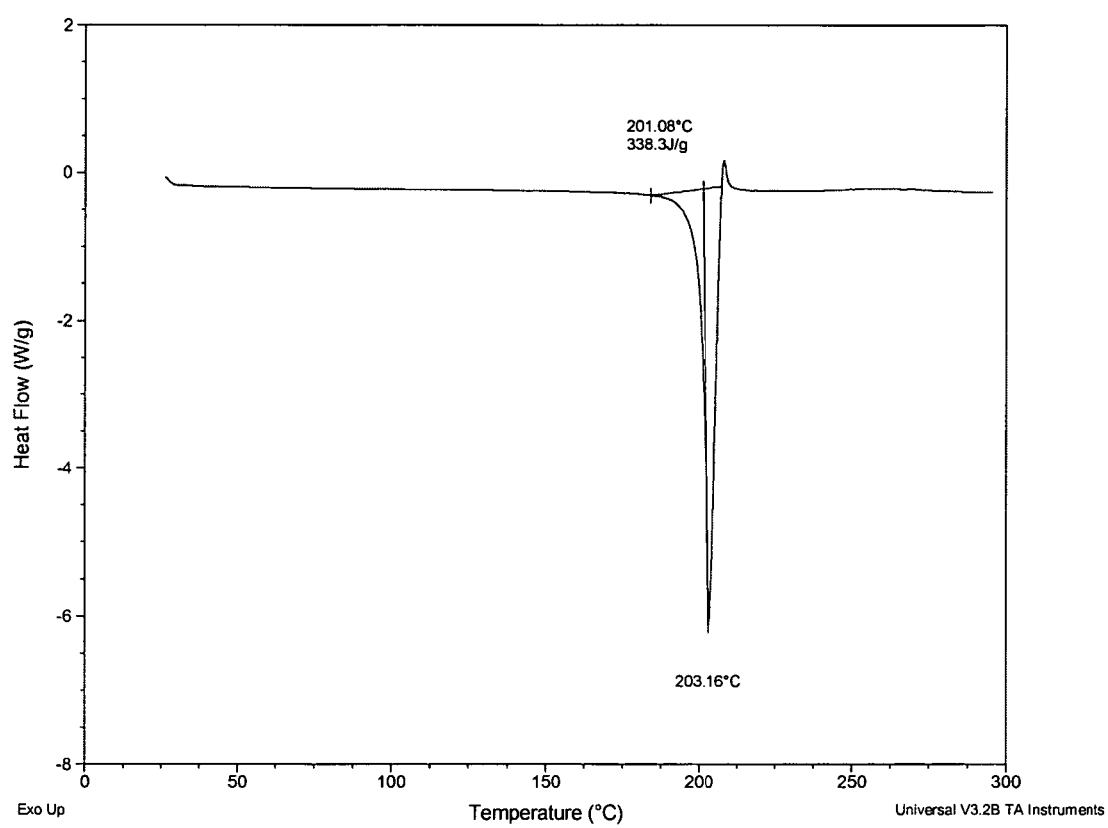
FIG. 2 is a characteristic differential scanning calorimetry thermogram of 3-{(3R,4R)-4-methyl-3-[methyl-(7H-pyrrolo[2,3-d]pyrimidin4-yl)-amino]-piperidin-1-yl}-3-oxo-propionitrile mono citrate salt. (Scan Rate: 5° C. per minute; Vertical Axis: Heat Flow (w/g); Horizontal Axis: Temperature (° C.)).

The crystalline form of the compound of this invention 3-{4-methyl-3-[methyl-(7H-pyrrolo[2,3-d]pyrimidin-4-yl)-amino]-piperidin-1-yl}-3-oxo-propionitrile mono citrate salt is prepared as described below.

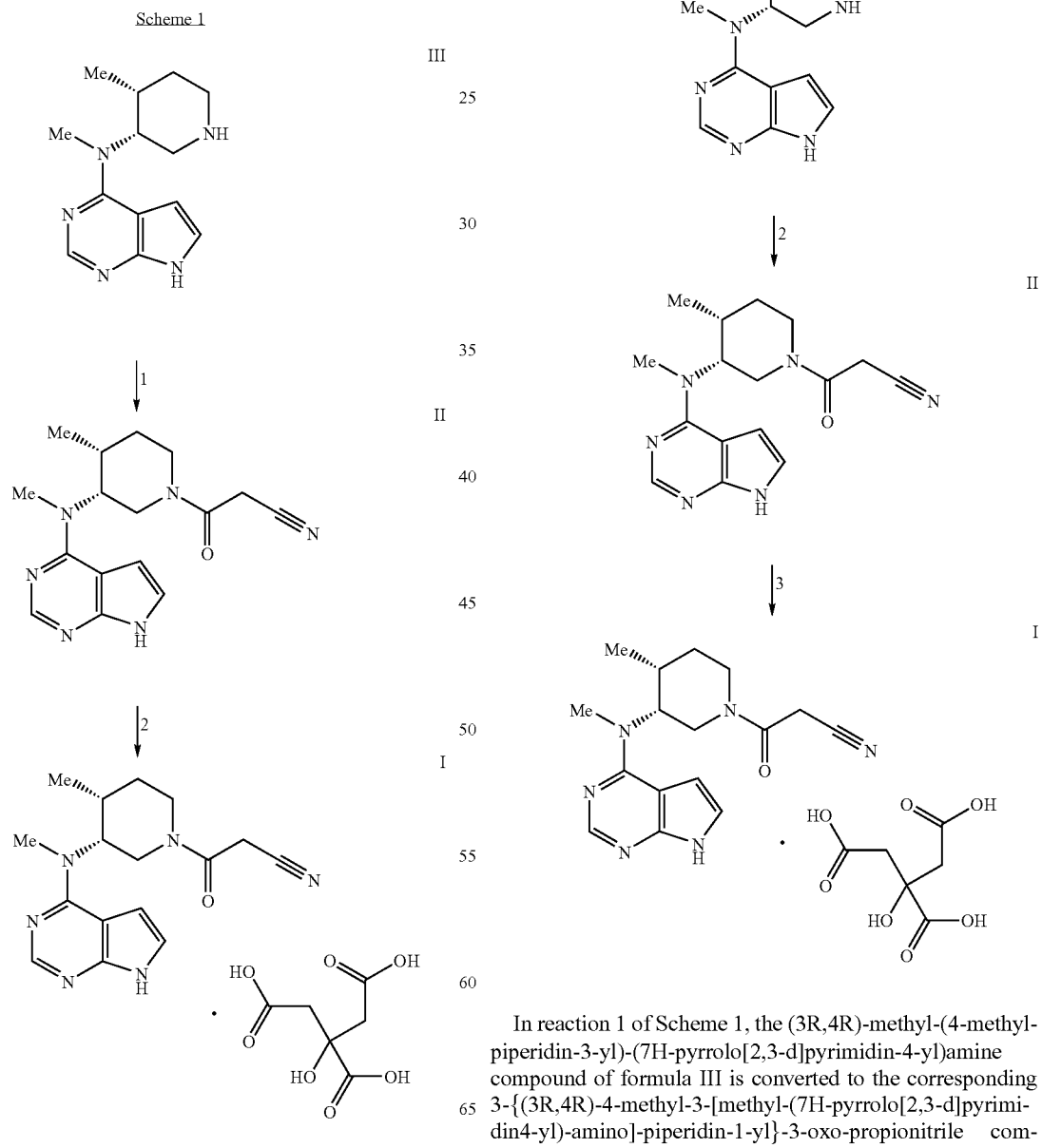

In reaction 1 of Scheme 1, the (3R,4R)-methyl-(4-methyl-piperidin-3-yl)-(7H-pyrrolo[2,3-d]pyrimidin-4-yl)amine compound of formula III is converted to the corresponding 3-{(3R,4R)-4-methyl-3-[methyl-(7H-pyrrolo[2,3-d]pyrimidin4-yl)-amino]-piperidin-1-yl}-3-oxo-propionitrile compound of formula II by reacting III with cyano-acetic acid 2,5-dioxo-pyrrolidin-1-yl ester in the presence of a base, such as triethylamine. The reaction mixture is stirred, at room temperature, for a time period between about 15 minutes to about 2 hours, preferably about 30 minutes.

In reaction 2 of Scheme I, the 3-{(3R,4R)-4-methyl-3-[methyl-(7H-pyrrolo[2,3-d]pyrimidin-4-yl)-amino]-piperidin-1-yl}-3-oxo-propionitrile compound of formula II is converted to the corresponding 3-{(3R,4R)-4-methyl-3-[methyl-(7H-pyrrolo[2,3-d]pyrimidin-4-yl)-amino]-piperidin-1-yl}-3-oxo-propionitrile mono citrate salt compound of formula I by reacting II with aqueous citric acid.

In reaction 1 of Scheme 2, the ((3R,4R)-1-benzyl-4-methyl-piperidin-3-yl)-methyl-(7H-pyrrolo[2,3-d]pyrimidin-4-yl)-amine compound of formula IV is converted tot the corresponding the (3R,4R)-methyl-(4-methyl-piperidin-3-yl)-(7H-pyrrolo[2,3-d]pyrimidin-4-yl)amine compound of formula III by treating IV with hydrogen in the presence of 20% palladium hydroxide on carbon (50% water by weight) and a polar protic solvent, such as ethanol. The reaction mixture is stirred at a temperature between about 45° C. to about 75° C., preferably about 60° C., under a pressure of about 60 psi, preferably about 50 psi, for a time period between about two days to about four days, preferably about three days.

In reaction 2 of Scheme 2, the (3R,4R)-methyl-(4-methyl-piperidin-3-yl)-(7H-pyrrolo[2,3-d]pyrimidin-4-yl)amine compound of formula III is converted to the corresponding 3-{(3R,4R)-4-methyl-3-[methyl-(7H-pyrrolo[2,3-d]pyrimidin-4-yl)-amino]-piperidin-1-yl}-3-oxo-propionitrile compound of formula II by reaction III with cyano-acetic acid 2,5-dioxo-pyrrolidin-1-yl ester in the presence of a polar protic solvent, such as ethanol. The reaction mixture is stirred, at room temperature, for a time period between about 30 minutes to about 3 hours, preferably about 1 hour.

In reaction 3 of Scheme 2, the 3-{(3R,4R)-4-methyl-3-[methyl-(7H-pyrrolo[2,3-d]pyrimidin-4-yl)-amino]-piperidin-1-yl}-3-oxo-propionitrile compound of formula II is converted to the corresponding 3-{(3R,4R)-4-methyl-3-[methyl-(7H-pyrrolo[2,3-d]pyrimidin-4-yl)-amino]-piperidin-1-yl}-3-oxo-propionitrile mono citrate salt compound of formula I by reacting II with citric acid in the presence of a polar solvent, such as acetone. The reaction mixture is stirred at a, temperature between about 30° C. to about 50° C., preferably about 40° C., for a time period between about 1 hour to about 3 hours, preferably about 2 hours. The resulting reaction mixture may optionally be further stirred at a temperature between about 20° C. to about 40° C., preferably about 30° C., for a time period between about 3 hours to about 5 hours, preferably about 4 hours, followed by additional stirring, at room temperature, for a time period between about 16 hours to about 20 hours, preferably about 18 hours.

The compositions of the present invention may be formulated in a conventional manner using one or more pharmaceutically acceptable carriers.

For oral administration, the pharmaceutical compositions may take the form of tablets prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art.

A proposed dose of the active compounds of the invention for oral, parenteral or buccal administration to the average adult human for the treatment of the conditions referred to above (e.g., rheumatoid arthritis) is 0.1 to 1000 mg of the active ingredient per unit dose which could be administered, for example, 1 to 4 times per day.

A compound of formula I administered in a pharmaceutically acceptable form either alone or in combination with one or more additional agents which modulate a mammlian immune system or with antiinflammatory agents, agents which may include but are not limited to cyclosporin A (e.g. Sandimmune® or Neoral®, rapamycin, FK-506 (tacrolimus), leflunomide, deoxyspergualin, mycophenolate (e.g. Cellcept®), azathioprine (e.g. Imuran®), daclizumab (e.g. Zenapax®), OKT3 (e.g. Orthocolone®), AtGam, aspirin, acctaminophen, ibuprofen, naproxen, piroxicam, and antiinflmmatory steroids (e.g. prednisolone or dexamethasone); and such agents may be administered as part of the same or separate dosage forms, via the same or different routes of administration, and on the same or different administration schedules according to standard pharmaceutical practice.

FK506 (Tacrolimus) is given orally at 0.10-0.15 mg/kg body weight, every 12 hours, within first 48 hours postoperative. Dose is monitored by serum Tacrolimus trough levels.

Cyclosporin A (Sandimmune oral or intravenous formulation, or Neoral®, oral solution or capsules) is given orally at 5 mg/kg body weight, every 12 hours within 48 hours postoperative. Dose is monitored by blood Cyclosporin A trough levels.

The active agents can be formulated for sustained delivery according to methods well known to those of ordinary skill in the art. Examples of such formulations can be found in U.S. Pat. Nos. 3,538,214, 4,060,598, 4,173,626, 3,119,742, and 3,492,397.

The ability of the compound of formula I; to inhibit Janus Kinase 3 and, consequently, demonstrate its effectiveness for treating disorders or conditions characterized by Janus Kinase 3 is shown by the following in vitro assay tests.

BIOLOGICAL ASSAY

JAK3 (JH1:GST) Enzymatic Assay

The JAK3 kinase assay utilizes a protein expressed in baculovirus-infected SF9 cells (a fusion protein of GST and the catalytic domain of human JAK3) purified by affinity chromatography on glutathione-Sepaharose. The substrate for the reaction is poly-Glutamic acid-Tyrosine (PGT (4:1), Sigma catalog # P0275), coated onto Nunc Maxi Sorp plates at 100 µg/ml overnight at 37° C. The morning after coating, the plates are washed three times and JAK3 is added to the wells containing 100 µl of kinase buffer (50 mM HEPES, pH 7.3, 125 mM NaCl, 24 mM MgCl2)+0.2 uM ATP+1 mM Na orthovanadate.) The reaction proceeds for 30 minutes at room temperature and the plates is washed three more times. The level of phosphorylated tyrosine in a given well is quantitated by standard ELISA assay utilizing an anti-phosphotyrosine antibody (ICN PY20, cat. #69-151-1).

Inhibition of Human IL-2 Dependent T-Cell Blast Proliferation

This screen measures the inhibitory effect of compounds on IL-2 dependent T-Cell blast proliferation in vitro. Since signaling through the IL-2 receptor requires JAK-3, cell active inhibitors of JAK-3 should inhibit IL-2 dependent T-Cell blast proliferation.

The cells for this assay are isolated from fresh human blood. After separation of the mononuclear cells using Accuspin System-Histopaque-1077 (Sigma # A7054), primary human T-Cells are isolated by negative selection using Lympho-Kwik T (One Lambda, Inc., Cat # LK-50T). T-Cells are cultured at 1-2×10$^6$/ml in Media (RPMI+10% heat-inactivated fetal calf serum (Hyclone Cat # A-1111-L)+1% Penicillin/Streptomycin (Gibco)) and induce to proliferate by the addition of 10 ug/ml PHA (Murex Diagnostics, Cat # HA 16). After 3 days at 37° C. in 5% CO$_2$, cells are washed 3 times in Media, resuspended to a density of 1-2×10$^6$ cells/ml in Media plus 100 Units/ml of human recombinant IL-2 (R&D Systems, Cat # 202-IL). After 1 week the cells are IL-2 dependent and can be maintained for up to 3 weeks by feeding twice weekly with equal volumes of Media+100 Units/ml of IL-2.

To assay for a test compounds ability to inhibit IL-2 dependent T-Cell proliferation, IL-2 dependent cells are washed 3 times, resuspended in media and then plated (50,000 cells/well/0.1 ml) in a Flat-bottom 96-well microtiter plate (Falcon #353075). From a 10 mM stock of test compound in DMSO, serial 2-fold dilutions of compound are added in triplicate wells starting at 10 uM. After one hour, 10 Units/ml of IL-2 is added to each test well. Plates are then incubated at 37° C., 5% CO$_2$ for 72 hours. Plates are then pulsed with $^3$H-thymidine (0.5 uCi/well) (NEN Cat # NET-027A), and incubated an additional 18 hours. Culture plates are then harvested with a 96-well plate harvester and the amount of $^3$H-thymidine incorporated into proliferating cells is determined by counting on a Packard Top Count scintillation counter. Data is analyzed by plotting the % inhibition of proliferation verses the concentration of test compound. An IC$_{50}$ value (uM) is determined from this plot.

The following Examples illustrate the preparation of the compounds of the present invention but it is not limited to the details thereof. Melting points are uncorrected. NMR data are reported in parts per million (δ) and are referenced to the deuterium lock signal from the sample solvent (deuteriochloroform unless otherwise specified).

EXAMPLE 1

3-{(3R,4R)-4-methyl-3-[methyl-(7H-pyrrolo[2,3-d]pyrimidin-4-yl)-amino]-piperidin-1-yl}-3-oxo-propionitrile mono citrate salt Ethanol (13 liters), (3R, 4R)-methyl-(4-methyl-piperidin-3-yl)-(7H-pyrrolo[2,3-d]pyrimidin-4-yl)-amine (1.3 kg), cyano-acetic acid 2,5-dioxo-pyrrolidin-1-yl ester (1.5 kg), and triethylamine (1.5 liters) were combined and stirred at ambient temperature. Upon reaction completion (determined by High Pressure Liquid Chromotography (HPLC) analysis, approximately 30 minutes), the solution was filtered, concentrated and azeotroped with 15 liters of methylene chloride. The reaction mixture was washed sequentially with 12 liters of 0.5 N sodium hydroxide solution, 12 liters of brine and 12 liters of water. The organic layer was concentrated and azeotroped with 3 liters of acetone (final pot temperature was 42° C.). The resulting solution was cooled to 20° C. to 25° C. followed by addition of 10 liters of acetone. This solution was filtered and then aqueous citric acid (0.8 kg in 4 liters of water) added via in-line filter. The reaction mixture was allowed to granulate. The slurry was cooled before collecting the solids by filtration. The solids were dried to yield 1.9 kg (71%) (3R, 4R)-3-{4-Methyl-3-[methyl-(7H-pyrrolo[2,3-d]pyrimidin-4-yl)-amino]-piperidin-1-yl}-3-oxo-propionitrile mono citrate. This material was then combined with 15 liters of a 1:1 ratio of ethanol/water and the slurry was agitated overnight. The solids were filtered and dried to afford 1.7 kg (63% from (3R, 4R)-methyl-(4-methyl-piperidin-3-yl)-(7H-pyrrolo[2,3-d]pyrimidin-4-yl)-amine) of the title compound as a white crystalline solid.

$^1$H NMR (400 MHZ)(D$_2$O) δHOD: 0.92 (2H, d, J=7.2 Hz), 0.96 (1H, d, J=7.6 Hz), 1.66 (1H, m), 1.80 (1H, m), 2.37 (1H, m), 2.58 (2H, ½ ABq, J=15.4 Hz), 2.70 (2H, ½ ABq, J=154 Hz), 3.23 (2H, s), 3.25 (1H, s), 3.33 (1H, m), 3.46 (1H, m), 3.81 (4H, m), 4.55 (1H, m), 6.65 (1H, d, J=3.2Hz), 7.20 (1H, t, J=3.2 Hz), 8.09 (1H, m).

EXAMPLE 2

3-{(3R,4R)-4-methyl-3-[methyl-(7H-pyrrolo[2,3-d]pyrimidin-4-yl)-amino]-piperidin-1-yl}-3-oxo-propionitrile mono citrate salt To a solution of 79 grams of ((3R, 4R)-1-Benzyl-4-methyl-piperidin-3-yl)-methyl-(7H-pyrrolo[2,3-d]pyrimidin-4-yl)-amine dissolved in 2 liters of ethanol was added 79 grams of 20% palladium hydroxide on carbon (50% water by weight) and the mixture agitated under an atmospheric pressure of 50 psi hydrogen for three days (conducting the hydrogenolysis at elevated temperature [50° C. to 70° C.] significantly decreases reaction times). After the catalyst was removed by filtration through Celite®, 51 grams of cyano-acetic acid 2,5-dioxo-pyrrolidin-1-yl ester was added to the ethanolic solution and the resulting mixture stirred at room temperature for 1 hour, at which time the ethanol was removed under reduced pressure. The residue was redissolved in 1.0 liters of dichloromethane and the solution sequentially washed with 0.6 liters of saturated aqueous sodium bicarbonate and 0.4 liters saturated sodium bicarbonate. The combined aqueous layers were backwashed with 0.4 liters of dichloromethane, the dichloromethane layers combined, dried over magnesium sulfate, filtered and concentrated in vacuo affording 61 grams of amber oil. This material was then redissolved in 2.1 liters of acetone and the solution heated to 40° C. Finely ground citric acid (37 grams) was added slowly (as a solid) to the solution. The mixture continued stirring at 40° C. for two hours (granulation was complete). After cooling to room temperature, the solids were collected by filtration, washed with acetone and dried in vacuo affording 78.5 grams (66% from ((3R, 4R)-1-Benzyl-4-methyl-piperidin-3-yl)-methyl-(7H-pyrrolo[2,3-d]pyrimidin-4-yl)-amine) of the title compound as a slightly off-white crystalline solid.

EXAMPLE 3

3-{(3R,4R)-4-methyl-3-[methyl-(7H-pyrrolo[2,3-d]pyrimidin-4-yl)-amino]-piperidin-1-yl}-3-oxo-propionitrile mono citrate salt A stirred solution of (3R,4R)-3-{4-Methyl-3-[methyl-(7H-pyrrolo[2,3-d]pyrimidin-4-yl)-amino]-piperidin-1-yl}-3-oxo-propionitrile (230 mg/0.74 mmol) dissolved in 23 mL of acetone was heated to 40° C. To this solution was added 155 mg (0.81 mmol) of finely ground citric acid. The resulting mixture stirred at 40° C. for 2 hours, then at 30° C. for 4 hours followed by stirring at room temperature for an additional 18 hours. At this point, the solids were collected by filtration, washed with acetone and dried in vacuo affording 280 mg (75%) of the title compound as a white crystalline solid.

EXAMPLE 4

Method for Collecting Powder X-ray Diffraction for 3-{(3R,4R)-4-methyl-3-[methyl-(7H-pyrrolo[2,3-d]pyrimidin-4-yl)-amino]-piperidin-1-yl}-3-oxo-propionitrile mono citrate salt Powder x-ray diffraction patterns for 3-{(3R,4R)4-methyl-3-[methyl-(7H-pyrrolo[2,3-d]pyrimidin-4-yl)-amino]-piperidin-1-yl}-3-oxo-propionitrile mono citrate salt were collected using a Bruker D5000 diffractometer (Madison, Wis.) equipped with copper radiation, fixed slits (1.0, 1.0, 0.6 mm) and a Kevex solid state detector. Data was collected as follows: Cu anode; wavelength 1: 1.54056; wavelength 2: 1.54439 (rel. intensity: 0.500); from 3.0 to 40.0 degrees in 2 theta using a step size of 0.04 degrees and a step time of 1.0 seconds. The results are summarized in Table 1.

TABLE 1

List of Powder X-ray Diffraction Peaks (±0.2 degrees)

| Angle 2-theta | d-value angstrom | Intensity* (rel.) % |
|---|---|---|
| 5.7 | 15.4 | 62.4 |
| 7.7 | 11.5 | 7.5 |
| 8.9 | 9.9 | 6.8 |
| 11.0 | 8.0 | 7.7 |
| 11.5 | 7.7 | 9.7 |
| 13.6 | 6.5 | 13.7 |
| 13.9 | 6.4 | 19.6 |
| 14.8 | 6.0 | 38 |
| 15.2 | 5.8 | 42.4 |
| 16.1 | 5.5 | 87.8 |
| 16.6 | 5.3 | 11.4 |
| 17.3 | 5.1 | 50.8 |
| 18.7 | 4.7 | 49.7 |
| 20.2 | 4.4 | 100 |
| 20.5 | 4.3 | 59.4 |
| 21.1 | 4.2 | 46.7 |
| 21.4 | 4.1 | 24 |
| 22.0 | 4.0 | 46.5 |
| 23.0 | 3.9 | 7.5 |
| 23.4 | 3.8 | 12.8 |
| 24.0 | 3.7 | 6 |
| 25.0 | 3.6 | 28.3 |
| 25.5 | 3.5 | 21.5 |
| 26.2 | 3.4 | 16.7 |
| 27.0 | 3.3 | 43.6 |
| 27.5 | 3.2 | 15.1 |
| 28.1 | 3.2 | 32.1 |
| 28.7 | 3.1 | 12.6 |
| 29.4 | 3.0 | 14.8 |
| 30.1 | 3.0 | 13.8 |
| 30.3 | 2.9 | 11 |
| 31.1 | 2.9 | 23.4 |
| 32.0 | 2.8 | 6.8 |
| 32.8 | 2.7 | 14.1 |
| 33.6 | 2.7 | 22.9 |
| 34.4 | 2.6 | 7.7 |
| 34.8 | 2.6 | 5.7 |
| 35.3 | 2.5 | 8.5 |
| 35.9 | 2.5 | 16.3 |
| 36.5 | 2.5 | 9.2 |
| 37.8 | 2.4 | 8.5 |
| 38.5 | 2.3 | 6.8 |
| 39.2 | 2.3 | 11.1 |

*The peak intensities may change depending on the crystal size and habit.

The invention claimed is:

1. A method for treating or preventing organ transplant rejection in a mammal, including a human, comprising administering to said mammal an amount of crystalline 3-{(3R,4R)-4-methyl-3-[methyl-(7H-pyrrolo[2,3-d]pyrimidin-4-yl)-amino]-piperidin-1-yl}-3-oxo-propionitrile mono citrate salt effective in treating or preventing organ transplant rejection.

2. The method of claim 1 wherein said crystalline 3-{(3R,4R)4-methyl-3-[methyl-(7H-pyrrolo[2,3-d]pyrimidin-4-yl)-amino]-piperidin-1-yl}-3-oxo-propionitrile mono citrate salt is characterized by an x-ray powder diffraction pattern having characteristic peaks expressed in degrees two-theta at approximately 5.7, 16.1, 20.2 and 20.5.

3. The method of claim 2 wherein said powder diffraction pattern has characteristic peaks expressed in degree of 2-theta at approximately:

| Angle 2-theta |
|---|
| 5.7 |
| 7.7 |
| 8.9 |
| 11.0 |
| 11.5 |
| 13.6 |
| 13.9 |
| 14.8 |
| 15.2 |
| 16.1 |
| 16.6 |
| 17.3 |
| 18.7 |
| 20.2 |
| 20.5 |
| 21.1 |
| 21.4 |
| 22.0 |
| 23.0 |
| 23.4 |
| 24.0 |
| 25.0 |
| 25.5 |
| 26.2 |
| 27.0 |
| 27.5 |
| 28.1 |
| 28.7 |
| 29.4 |
| 30.1 |
| 30.3 |
| 31.1 |
| 32.0 |
| 32.8 |
| 33.6 |
| 34.4 |
| 34.8 |
| 35.3 |
| 35.9 |
| 36.5 |
| 37.8 |
| 38.5 |
| 39.2. |

4. The method of claim 1 wherein said crystalline 3-{(3R,4R)-4-methyl-3-[methyl-(7H-pyrrolo[2,3-d]pyrimidin-4-yl)-amino]-piperidin-1-yl}-3-oxo-propionitrile mono citrate salt has an onset melting temperature of between about 199° C. to about 206° C.

5. A method for treating asthma in a mammal comprising administering to said mammal an amount of crystalline 3-{(3R,4R)-4-methyl-3-[methyl-(7H-pyrrolo[2,3-d]pyrimidin-4-yl)-amino]-piperidin-1-yl}-3-oxo-propionitrile mono citrate salt effective in treating asthma.

6. The method according to claim 5, wherein the crystalline 3-{(3R,4R)-4-methyl-3-[methyl-(7H-pyrrolo[2,3-d]pyrimidin-4-yl)-amino]-piperidin-1-yl}-3-oxo-propionitrile mono citrate salt is administered in combination with one or more of cyclosporin A, rapamycin, tacrolimus, leflunomide, deoxyspergualin, mycophenolate, azathioprine, daclizumab, muromonab-CD3, antithymocyte globulin, aspirin, acetaminophen, ibuprofen, naproxen, piroxicam, prednisolone or dexamethasone.

7. The method of claim 5 wherein said crystalline 3-{(3R,4R)-4-methyl-3-[methyl-(7H-pyrrolo[2,3-d]pyrimidin-4-yl)-amino]-piperidin-1-yl}-3-oxo-propionitrile mono citrate salt has an onset melting temperature of between about 199° C. to about 206° C.

8. The method of claim 5 wherein said crystalline 3-{(3R,4R)-4-methyl-3-[methyl-(7H-pyrrolo[2,3-d]pyrimidin-4-yl)-amino]-piperidin-1-yl}-3-oxo-propionitrile mono citrate salt is characterized by an x-ray powder diffraction pattern having characteristic peaks expressed in degrees two-theta at approximately 5.7, 16.1, 20.2 and 20.5.

9. The method of claim 8 wherein said powder diffraction pattern has characteristic peaks expressed in degree of 2-theta at approximately:

| Angle 2-theta |
| --- |
| 5.7 |
| 7.7 |
| 8.9 |
| 11.0 |
| 11.5 |
| 13.6 |
| 13.9 |
| 14.8 |
| 15.2 |
| 16.1 |
| 16.6 |
| 17.3 |
| 18.7 |
| 20.2 |
| 20.5 |
| 21.1 |
| 21.4 |
| 22.0 |
| 23.0 |
| 23.4 |
| 24.0 |
| 25.0 |
| 25.5 |
| 26.2 |
| 27.0 |
| 27.5 |
| 28.1 |
| 28.7 |
| 29.4 |
| 30.1 |
| 30.3 |
| 31.1 |
| 32.0 |
| 32.8 |
| 33.6 |
| 34.4 |
| 34.8 |
| 35.3 |
| 35.9 |
| 36.5 |
| 37.8 |
| 38.5 |
| 39.2. |

* * * * *